US005458418A

United States Patent [19]
Jones et al.

[11] Patent Number: 5,458,418
[45] Date of Patent: Oct. 17, 1995

[54] METHOD FOR DETECTING POOR MEAT QUALITY IN LIVE ANIMALS

[75] Inventors: Stephen D. M. Jones; Allan L. Schaefer; Alan K. Tong, all of Lacombe; Shannon L. Scott, Ste-Foy; Claude D. J. Gariepy, Otterburn Park; Richard C. Graham, Ottawa, all of Canada

[73] Assignee: Her Majesty The Queen In Right Of Canada as represented by the Minister of Agriculture, Lacombe, Canada

[21] Appl. No.: 84,993

[22] Filed: Jul. 2, 1993

[51] Int. Cl.⁶ .................................................. G01N 25/00
[52] U.S. Cl. ................................ 374/45; 374/124; 99/493
[58] Field of Search .............................. 374/45, 124, 4; 99/493

[56] References Cited

U.S. PATENT DOCUMENTS

| | | | |
|---|---|---|---|
| 3,877,818 | 4/1975 | Button et al. | 250/340 |
| 3,948,249 | 4/1976 | Ambrosini . | |
| 3,991,744 | 11/1976 | Goodfield . | |
| 4,366,381 | 12/1982 | Fischer et al. | 374/124 |
| 4,788,427 | 11/1988 | LeRoy | 374/124 |
| 4,914,672 | 4/1990 | Hebrank | 374/124 |
| 4,995,398 | 2/1991 | Turnidge | 128/736 |
| 4,998,826 | 3/1991 | Wood et al. | 374/124 |
| 5,017,019 | 5/1991 | Pompei | 374/133 |

FOREIGN PATENT DOCUMENTS

| | | |
|---|---|---|
| 91/14180 | 9/1991 | WIPO . |
| 92/00523 | 1/1992 | WIPO . |

OTHER PUBLICATIONS

Garry B. Desroches, "Stress Affected Livestock as Seen by Thermography", Proceedings of Internat'l Society for Optical Engineering 934: 120–129 (1988).
A. L. Schaeffer et al. "Infrared Thermography of Pigs with Known Genotypes for Stress Susceptibility in Relation to Pork Quality", Canadian Journal of Animal Science 69: 491–495 (1989).
Schaefer, A. L., Jones, S. D. M., Tong, A. K. W. and Vincent, B. C. (1988). The effects of fasting and transporation on beef cattle. 1. Acid–base–electrolyte balance and infrared heat loss of beef cattle. Lives.Prod.Sic. 20:15–23.
Gariepy, C. J., Amiot. J. and Mada, S. (1987). Early prediction of PSE and DFD by infrared thermography on Live anmials. Proc. 33rd Int. Cong. Meat Sci. Tech. II 403–406.
Clark, J. A. and Cena, K. (1972). The application of thermovision techniques to animals. Deutsche Tierarztliche Wochen schrift. 79:292–296.
Lamarque, J. L., Senac, J. P., Rossi, M., Pasquel, J., Respand, G., Romieu, M. and Jiordan, J. (1975). Etudthermographique experimentale on pathologic artevielle peripherique. Ann. Radiol. 18:513–523.
Kenny, F. J. and Tarrant, P. V. (1987). The physiological and behavioural responses of crossbred Friesian Steers to short–haul transport by road. Lives.Prod.Sci. 17:63–75.
Stephens, D. B. (1980). Stress and its management in domestic animals: A review of behavioural and physiological studies under field and laboratory situations. Adv. Vet. Sci. Comp. Med. 24:179–210.
Frens, J. (1975). The influence of skin temperature on thermoregulation. In N. J. M. A. Tilburg, M G. Strasbourg and E. F. J. R. Both (Ed.) Thermography. S. Karger, Basel P. 218–223.

(List continued on next page.)

*Primary Examiner*—Diego F. F. Gutierrez
*Attorney, Agent, or Firm*—Finnegan, Henderson, Farabow, Garrett & Dunner

[57] ABSTRACT

The invention provides methods of detecting poor meat quality in live animals using infrared thermography. In cattle, animals whose thermographs are predominantly outside the test temperature range, 28°–32°±2° C., are rejected as having a high probability of producing poor meat quality. In swine, the test temperature range is 24°–26°±2° C.

20 Claims, 14 Drawing Sheets

OTHER PUBLICATIONS

Houdas, Y. and Guieu, J. D. (1975). Environmental Factors affecting skin temperatures. In. N. J. M. A. Tilburg, M. G. Strasbourg and E. F. J. R. Both (Ed.) Thermography. S. Karger, Basal pp. 157–165.

Jones, S. D. M., Schaefer, A. L., Tong, A. K. W. and Vincent, B. C. (1968). The effects of of fasting and transportation on beef cattle. 2. Body component changes, carcass composition and meat quality. Lives.Prod.Sci. 20:25–35.

Warris, P. (1986). Live animals marketing effects on carcass and meat quality. Proceedings P 7–41. In. Work Planning Meeting and meat quality. Agric.Can.R.P.S. Ottawa.

Scahefer, A. L. Jones, S. D. M., Tong, A. K. W. and Vincent, B. C. (1987)a. The effects of fasting and transport on acid–base balance, infrared heat loss and muscle quality of beef cattle. Can.J.Anim. 67:1182.

Schaefer, A. L., Jones, S. D. M., Murray, A. C., Sather, A. P. and Tong, A. K. W. (1987)b. Infrared thermography in three lines of pigs. Can.J.Anim.Sci. 67:1181–1182.

Hayward, J. A., Eckerson, J. D. and Collis, M. (1975). Thermal balance and survival time prediction of men in cold water. Can.J.Physiol.Pharmacol. 53:21–32.

Jones, S. D. M. and Tong, A. K. W. (1989). Factors influencing the commercial incidence of dark cutting. Can.J.Anim.Sci. 69:849–854.

Sather, A. P. and Murray, A. C. (1989). The development of a halothane sensitive line of pigs. Can.J.Anim.Sci. 69:323–331.

Murray, A. C. and Sather, A. P. (1986). Characteristics of the meat quality of a halothane–positive line of swine. Can.J.Anim.Sci. 56:1168.

Hayward, J. S., Collis, M. and Eckerson, J. D. (1973). Thermographic Evaluation of Relative Heat Loss Areas of Man During Cold Water Immersion. Aerospace Medicine Jul., 1973, pp. 708–711.

Gariepy, C., Schaefer, A. L., Newman, J. A., Jones, S. D. M. and Murray, A. C. (1969). Adipose tissue thermogenesis in halothane positive pigs. Can.J.Anim.Sci. 69:1130.

Scott, S. L., Schaefer, A. L., Jones, S. D. M. and Tong, A. K. W. (1991). What Effect Does Transportation Have on Heat Loss in Cattle? Lacombe Research Highlights 1991, 20–21.

Scott, S. L., Schaefer, A. L., Jones, S. D .M. and Tong, A. K. W. (1992). Assessment of the effect of transportation of heat loss in cattle by thermographic analysis. Can.Soc.Anim.Sci. Annual Meeting, Jul. 5–9, 1992.

Stephen, V. E. and Gorlach, A. (no date). Measurements of surface temperatures by infrared thermography in veterinary medicine (preliminiary report). Dtsch. tieraztl. Wachr. 78:330–332.

European Patent Application EP 0402877 A1 (1990) (Abstract only).

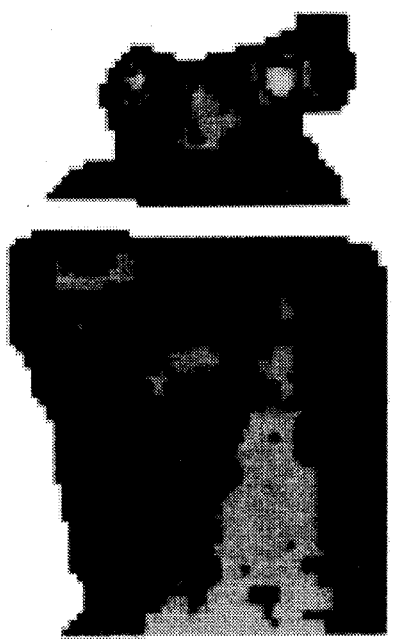
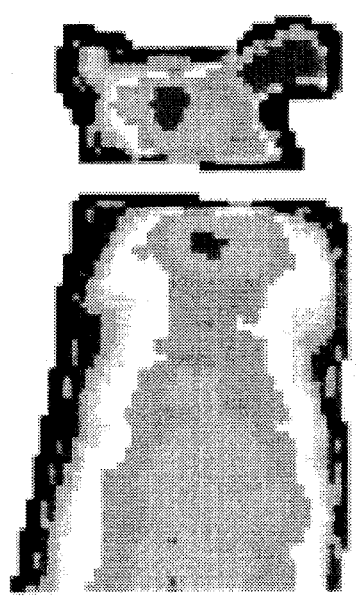
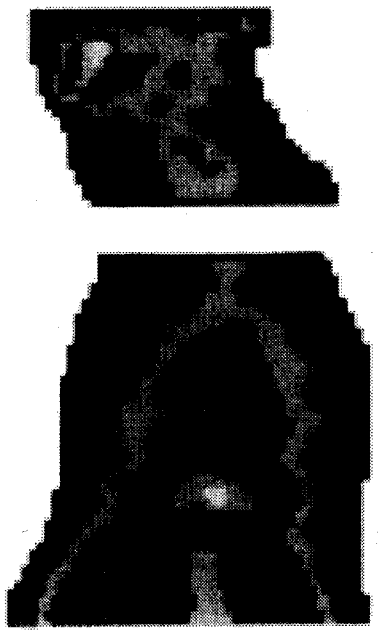
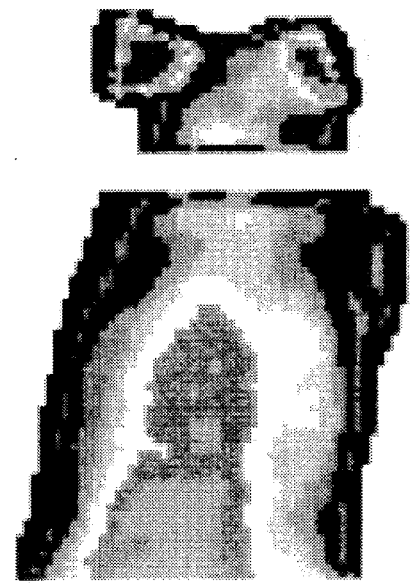
Fig. 5A.  Fig. 5B.

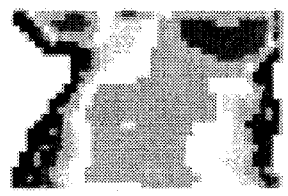
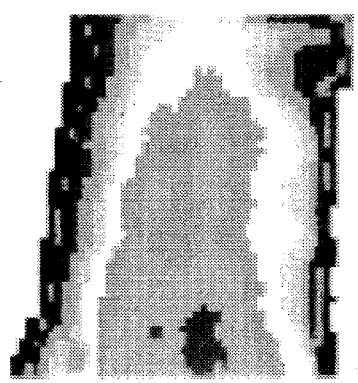
Fig. 6A.          Fig. 6B.

METHOD FOR DETECTING POOR MEAT QUALITY IN LIVE ANIMALS

FIELD OF THE INVENTION

This invention relates to methods for detecting poor meat quality in live animals, and more particularly to the use of infrared thermography for such purposes.

BACKGROUND OF THE INVENTION

In domestic livestock, handling and transport are known to be potent stressors (Stephens, 1980; and Kenny et al., 1987). Such stresses are often termed "antemortem stresses". These stresses have been documented to bring about changes in many physiological parameters including thermoregulation (Frens, 1975; and Houdas et al., 1975). It is also well documented that such factors as handling, mixing, and transport in the preslaughter environment (the "antemortem environment") are causative agents of poor meat quality (Jones et al., 1989; Jones et al., 1988; Warriss, 1986). Primarily affected are such quality attributes as colour, moisture holding capacity, pH, toughness and texture. If the stress is severe enough, the animal's energy supply is taxed, which in turn may lead to poor or degraded meat quality, such as dark, firm and dry (DFD) or tough meat in beef cattle, or pale, soft and exudative (PSE) meat in swine.

The assessment of meat quality has always, by necessity, been done on post mortem analysis. To the inventors' knowledge there has never been a technology with a demonstrated capability to detect animals likely to produce poor meat quality. Arguably, the development or discovery of such a technology capable of predicting meat quality in live animals in the antemortem environment would have significant value to the meat production industry, since preventative and restorative therapy could then be initiated in those identified animals.

Infrared thermography (IRT) has been used in human medicine for some time for the diagnosis and study of such conditions as tumors and cardiovascular integrity (Clark et al., 1972) as well as hyperthemia (Hayward et al., 1975). In domestic animals, IRT has also been found useful for diagnosing such conditions as vascular lesions in pigs (Lamarque et al., 1975) and leg injuries in horses (Clark et al., 1972).

The patent literature discloses the use of IRT for several purposes. U.S. Pat. No. 3,877,818 to Burton et al., discloses the use of IRT for determining fat content in meat (post mortem). U.S. Pat. No. 3,948,249 to Ambrosini teaches the use of an infrared detector for identifying a cow in heat. U.S. Pat. No. 5,017,019 to Pompei discloses the use of radiation detectors to measure temperature differentials in animals.

The inventors have been involved in previous studies using IRT with live animals. Initial studies by the co-inventors Jones, Schaefer and Gariepy suggested that IRT might be useful in identifying basic stress levels in cattle (Schaefer et al., 1987a, 1988) and in swine (Schaefer et al., 1987b; and Gariepy et al., 1987). The studies recognized that cattle having cooler surface temperatures as measured by IRT appear to have lower meat quality, while in pigs, poor meat quality was associated with very high surface temperature. However, these studies fell short of teaching a method for reliably detecting the likelihood of poor meat quality in live animals.

There is a need for a method for detecting, with acceptable accuracy, live animals susceptible to producing poor meat quality.

SUMMARY OF THE INVENTION

The inventors set out to develop a method for detecting poor meat quality in live animals with infrared thermography, by studying the anatomical sites and temperatures for different animals, along with the methods of analysing the thermographic data, so as to be sufficiently predictive of the relevant meat quality traits. By testing a large number of animals and breaking down the thermographic images by temperature zones, they discovered, surprisingly, that animals which went on to produce poor quality meat had infrared thermographs which were uncharacteristic in a particular test temperature zone. Compared to animals which produced high grade meat quality, the low grade meat quality animals were found to have thermographs which had higher proportions of the scan (measured by proportion of total pixel count) in temperature zones which were higher and lower than the test temperature zone. This discovery enabled the inventors to develop a reliable method for detecting for low meat quality in live animals.

Broadly stated, the invention provides a method for detecting a high probability of producing poor meat quality in live domestic livestock, comprising the steps of:

(a) scanning the live animal with an infrared camera to produce a thermographic image;

(b) for cattle, determining the proportion of the scan falling within the test temperature range of $28°–32°\pm2°$ C.;

(c) for swine, determining the proportion of the scan falling within the test temperature range of $24°–26°\pm2°$ C.; and (c) rejecting the animal as one having a high probability of producing poor meat quality if the proportion of the scan falling within the test temerature range is lower than that falling outside the test temperature range.

The term "livestock", as used herein and in the claims, is meant to include domestic ruminant and monogastric animals, including swine, horses, cattle (*Bos taurus* and *Bos indicus*) and domestic ungulates such as bison, sheep, lamb, deer, moose, elk, caribou and goats.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 5A, 5B, 6A and 6B are IR thermographs from four pigs before (A) and after (B) stresses approximating an antemortem environment;

DESCRIPTION OF THE PREFERRED EMBODIMENTS

Figure 1:
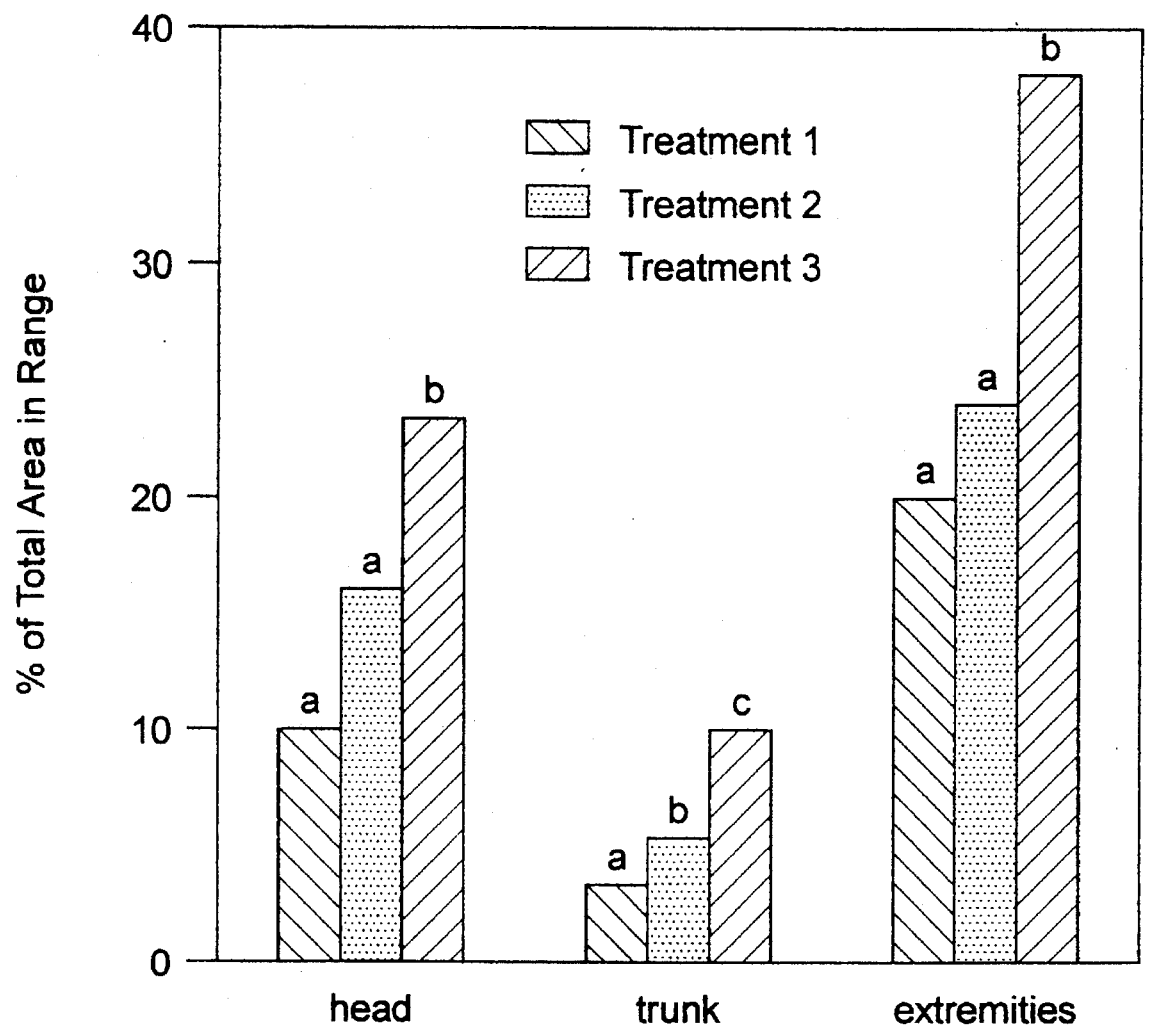
FIGS. 1–4 are histogram plots of four temperature ranges from infrared thermographs on three zones of cattle which had been subjected to antemortem stress.
Figure 2:
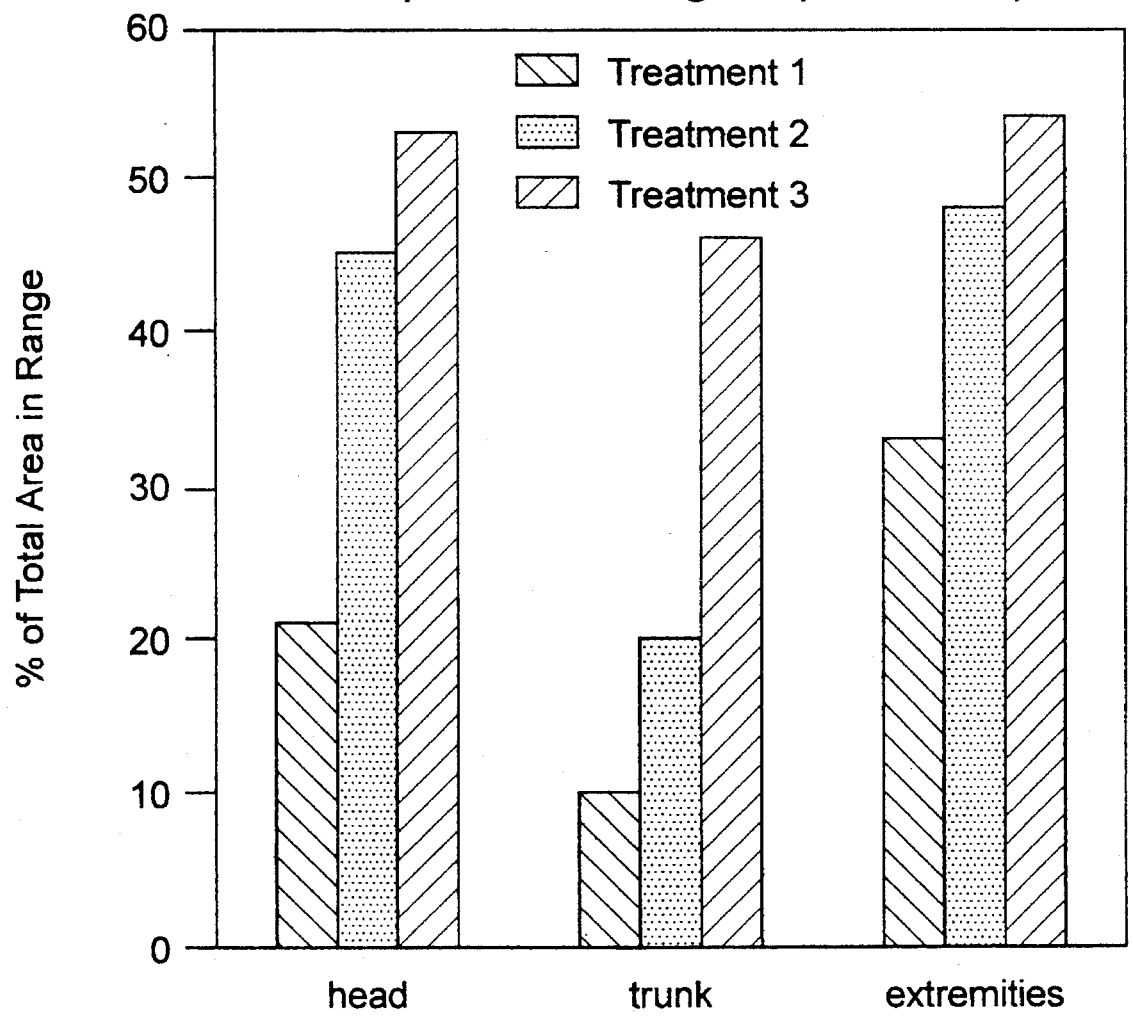
Figure 3:
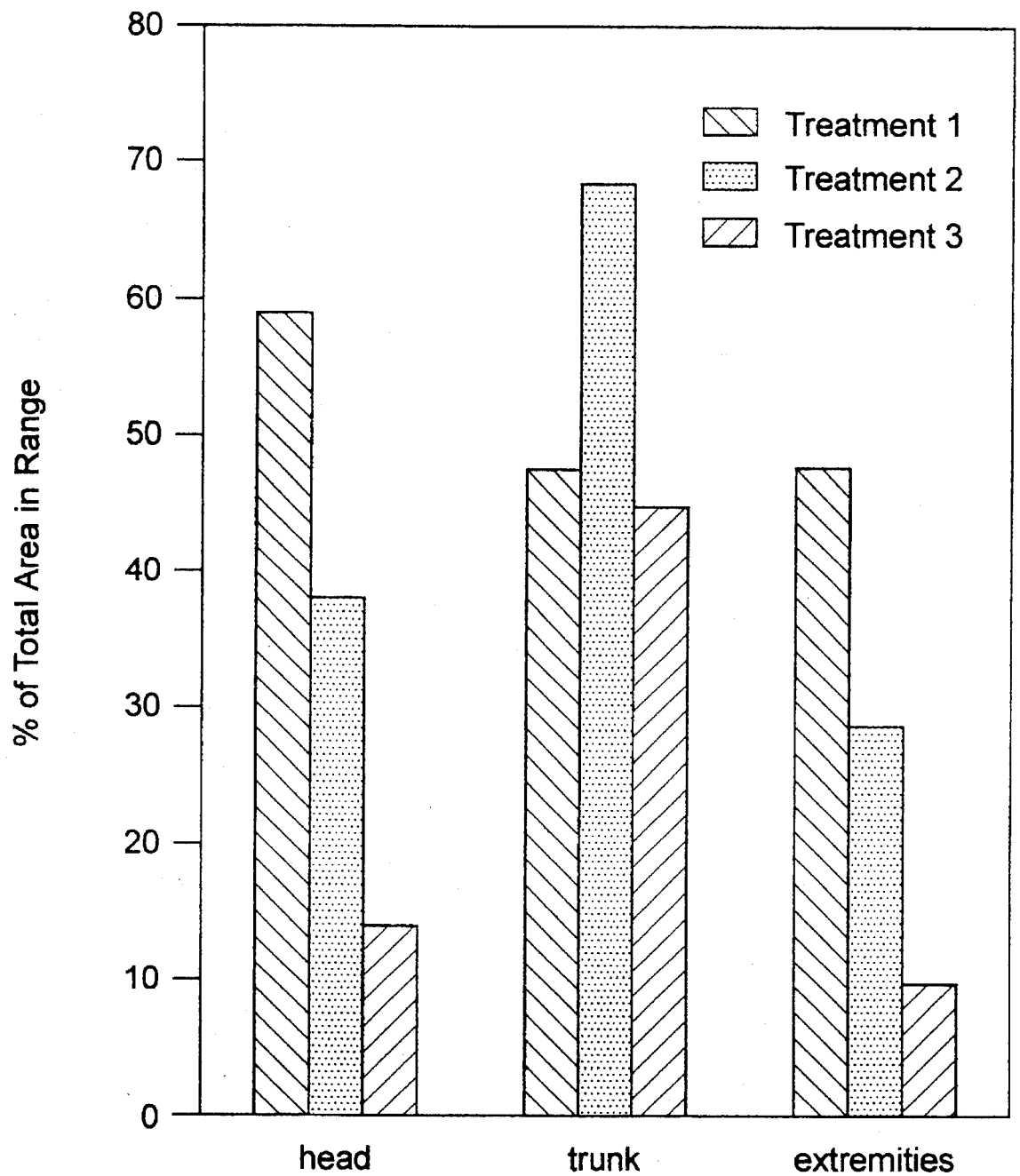
Figure 4:
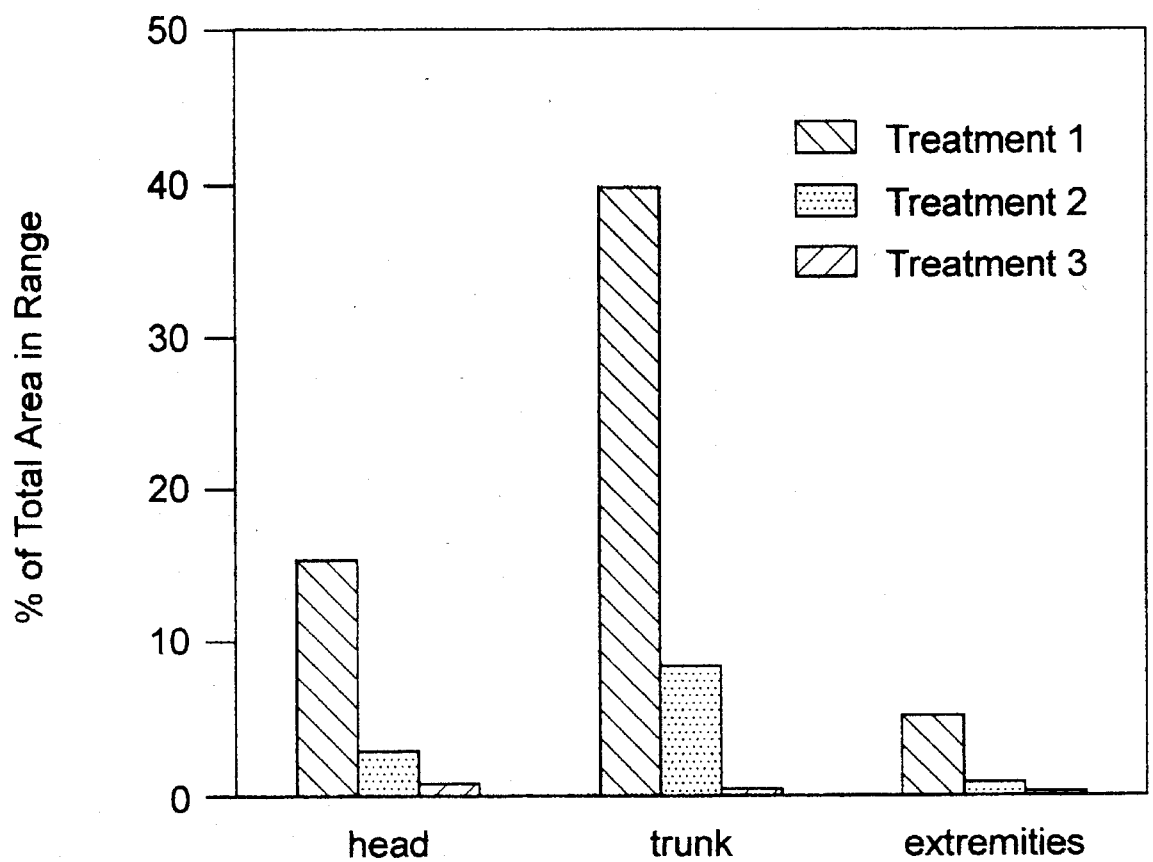
Figure 7:
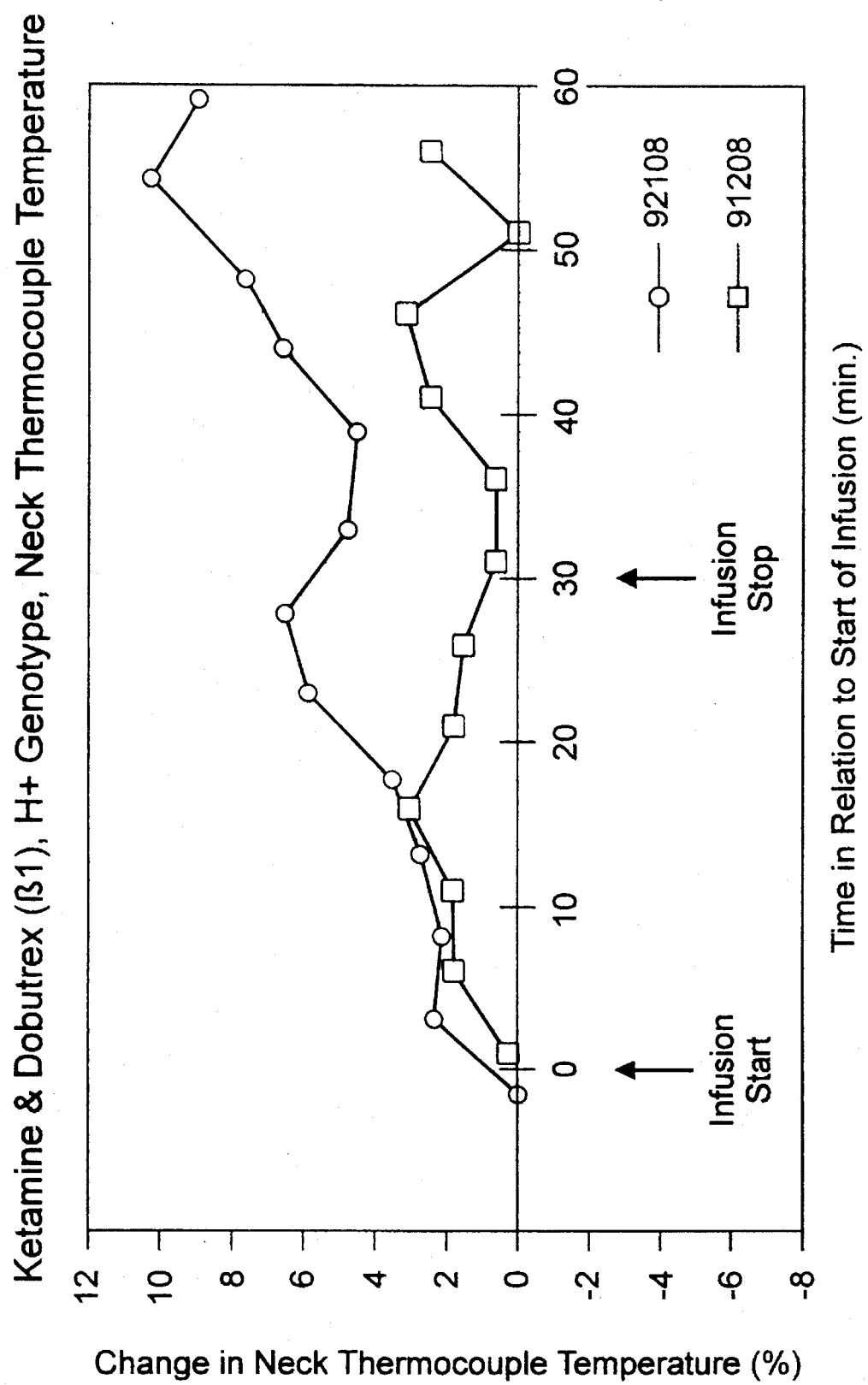
FIGS. 7–12 are plots of temperature vs. time for different anatomical sites on pigs during infusion of stress hormones.
Figure 8:
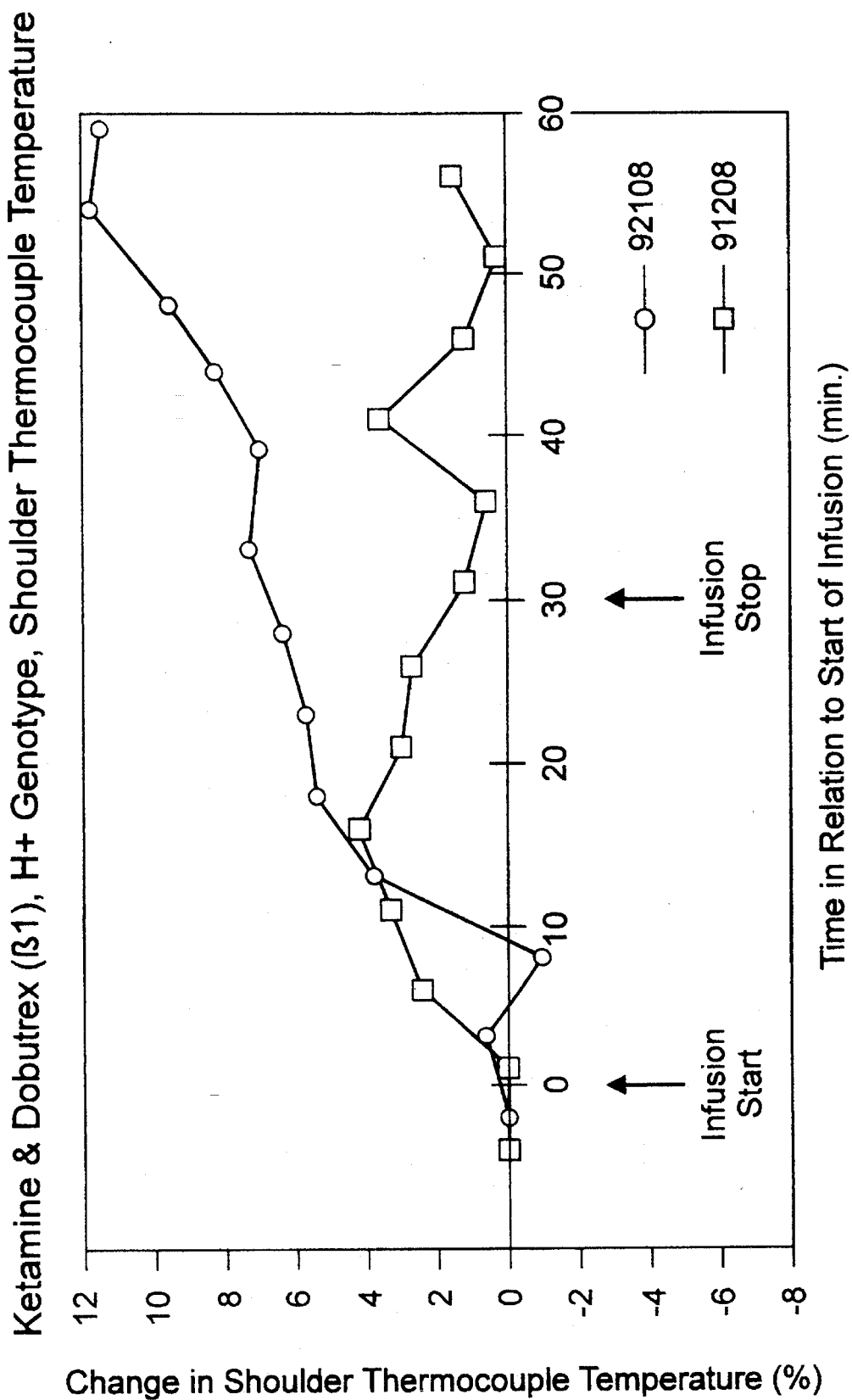
Figure 9:
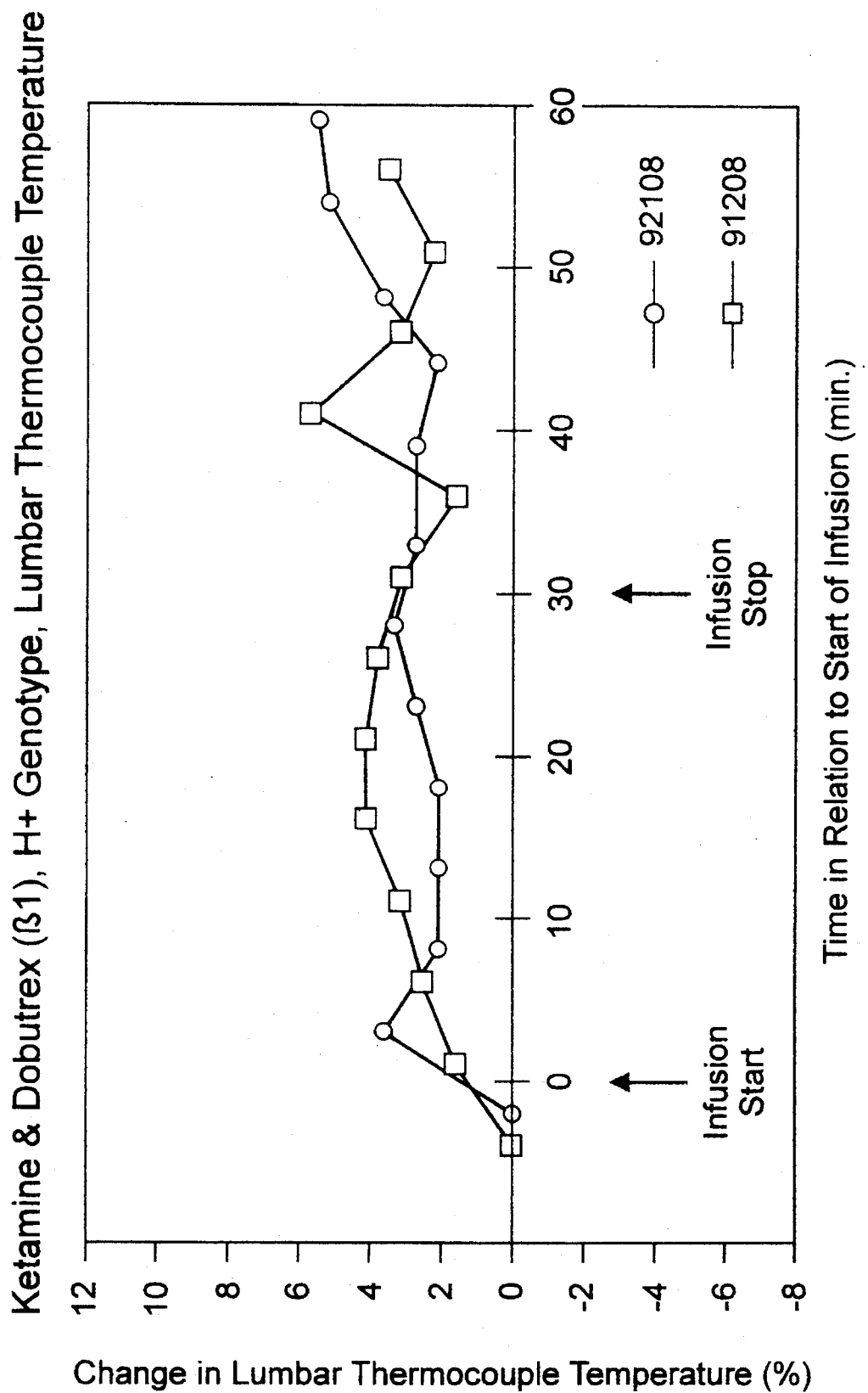
Figure 10:
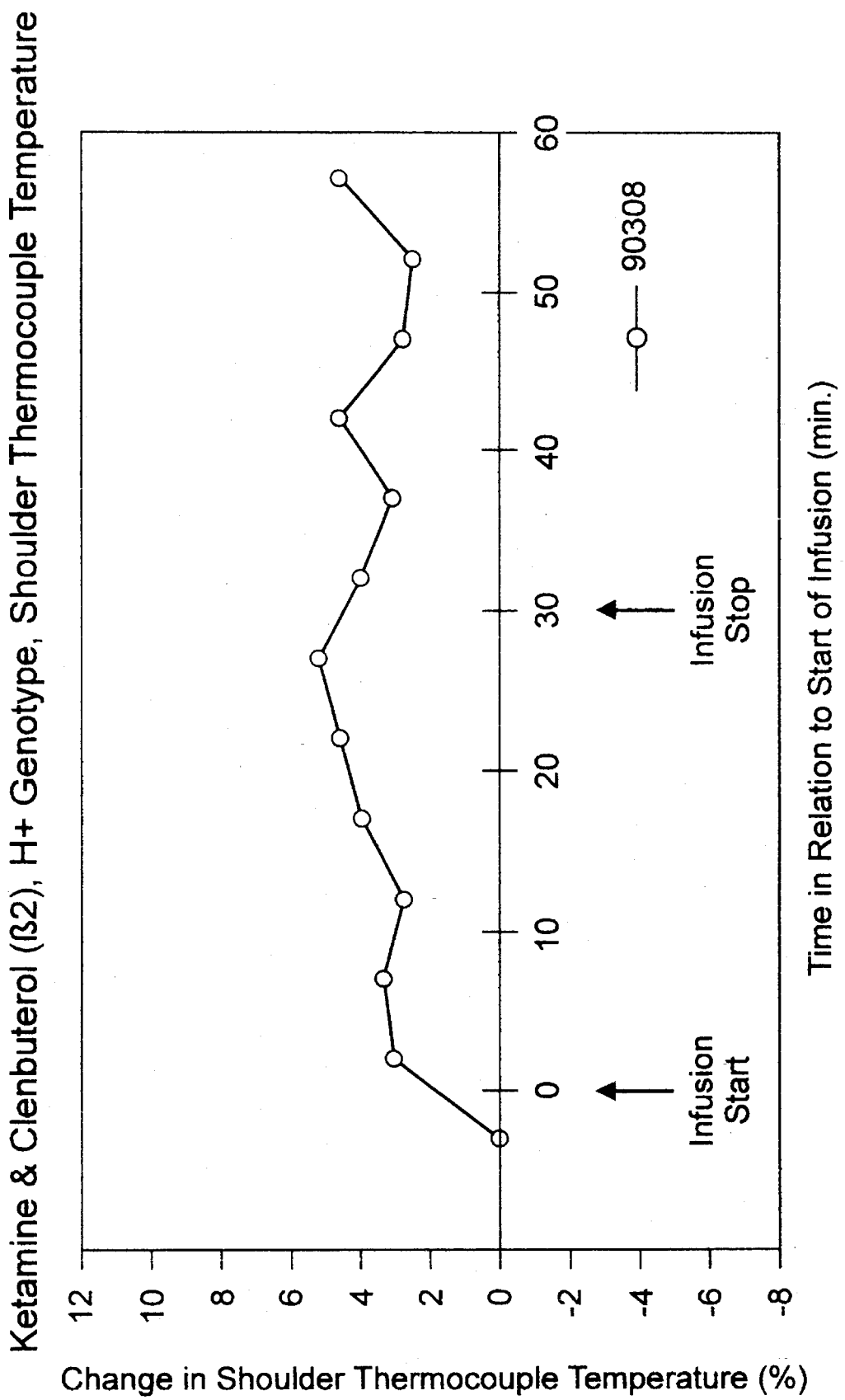
Figure 11:
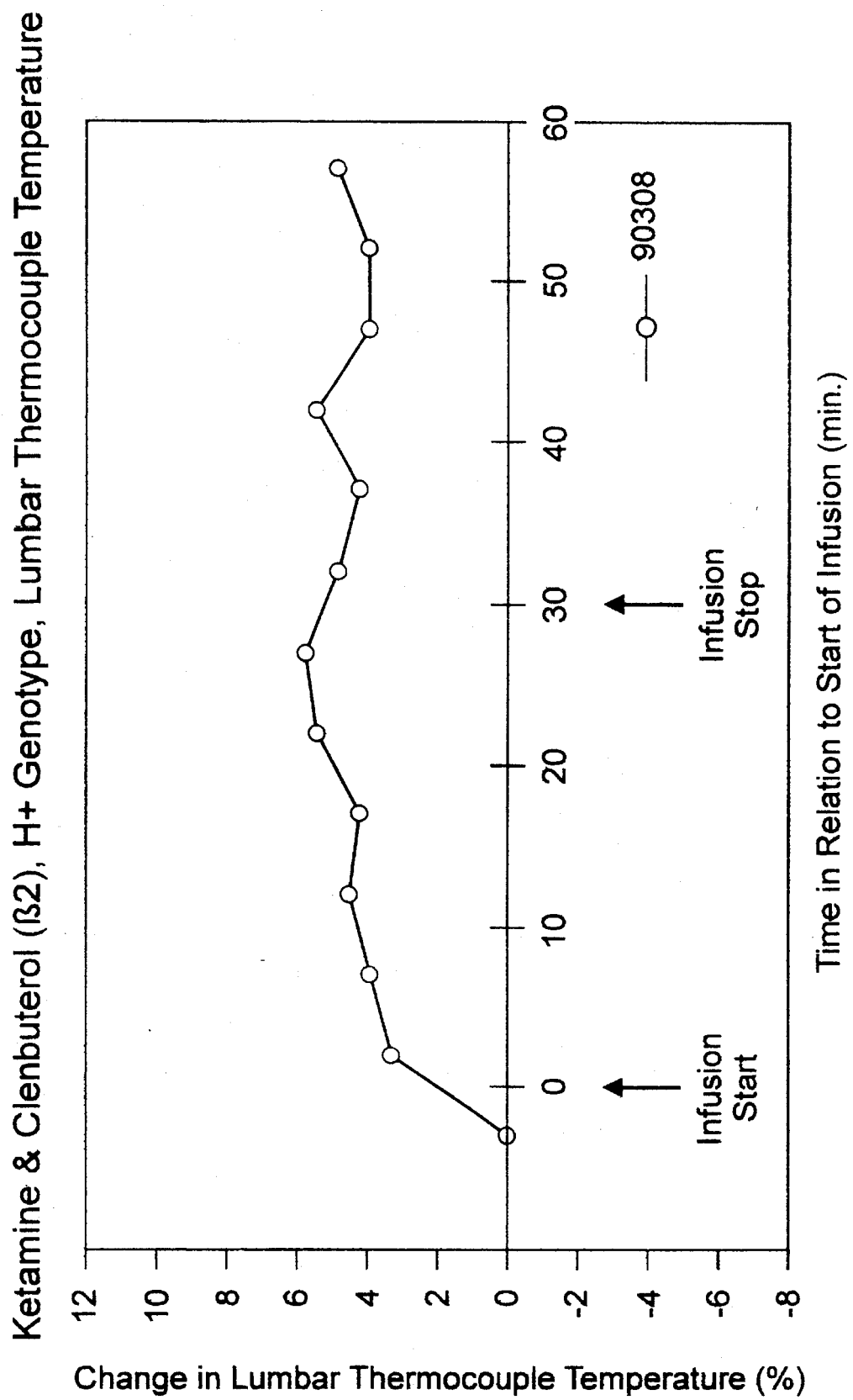
Figure 12:
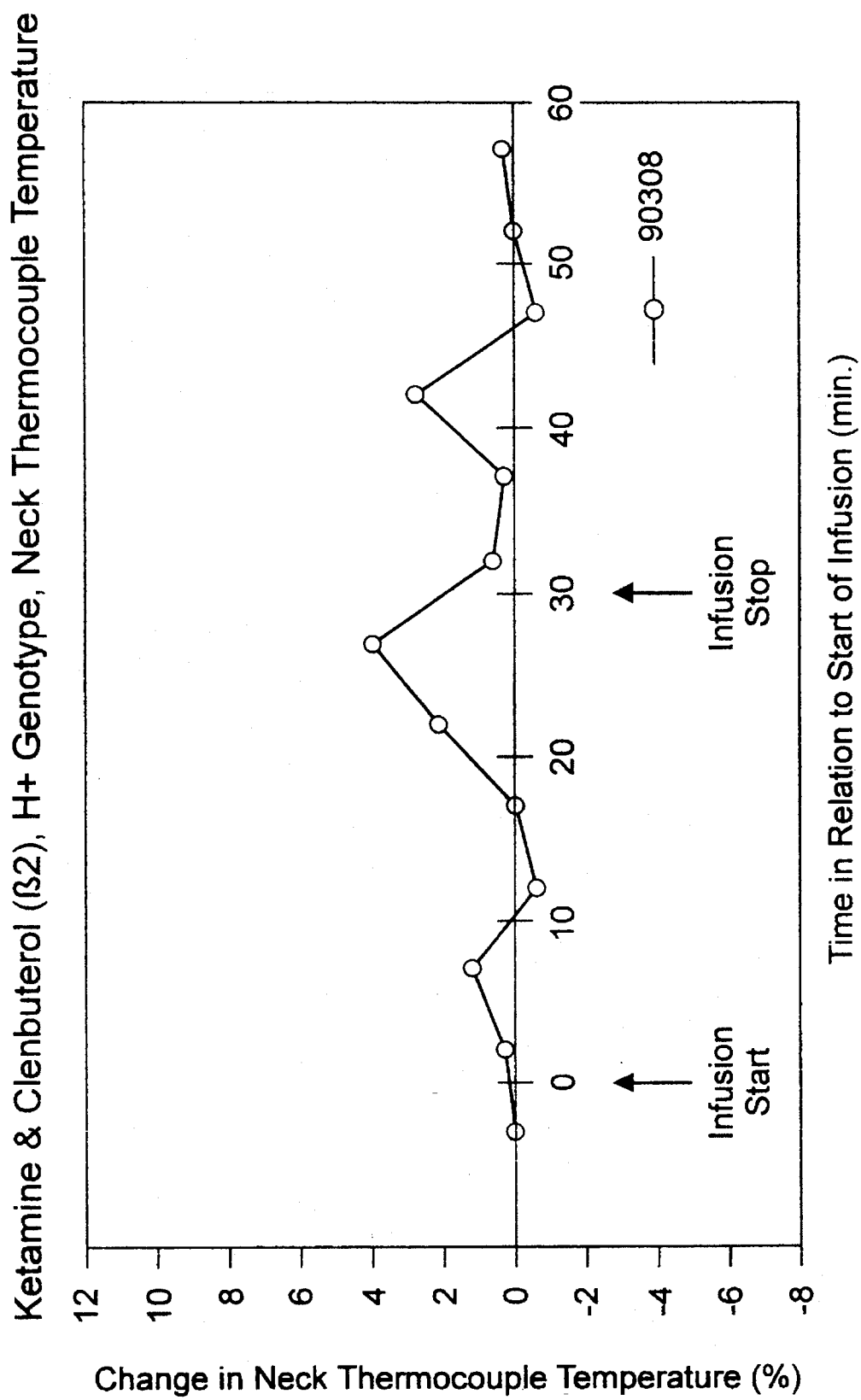

The method of the present invention has proven to be very effective in detecting domestic livestock with a high probability of producing poor or degraded meat quality on subsequent slaughter. In a test group of 54 bulls (Ex. 3), the method proved to be greater than 80% effective in advance detection of dark cutting. This is a very high accuracy rate. Once animals are detected, they may be treated to improve meat quality. For instance, a composition for such a method of restoring degraded meat quality and improving carcass yield loss is disclosed in pending U.S. application Ser. No. 08/084,989 filed Jul. 2, 1993 by Schaefer et al.

Infrared thermography equipment (camera, analytical software) is known in the art. Preferably, animals, or relevant anatomical sites, are scanned at relatively close range (1–3 m) at an angle between about 45°–90° from the horizontal surface of the animal.

Software is available for analysing the thermographic images produced from the camera. An exemplary software package is Viewsoft (Version 2.0 Viewscan Ltd., Concord, Ontario, Canada). The images are preferably analyzed to determine the proportion of a scan falling within a particular temperature range (i.e. proportion of total pixels of a defined area which falls within a particular temperature range).

In accordance with the invention, live animals are scanned with the camera. The thermographic image is analyzed (preferably by computer, but alternatively by visual analysis) to determine the proportion of the scan falling within a test temperature range. The test temperature range found to most efficaceous is 28°–32°±2° C. for cattle and 24°–26°±2° for swine (These temperature ranges may shift up or down by 2°, depending on the type of animal, the degree of stress and ambient temperature conditions affecting the normal body temperatures of animals). Normal body temperatures of animals should be set each day of scanning to allow for variation in the test range. Animals are detected as likely to have poor meat quality degradation if the proportion of the scan within the test temperature range is lower than that falling outside the test temperature range.

Preferred conditions of scanning have been worked out for different animal types, relevant anatomical sites, type of scan view, timing of the detection.

In general, the inventors discovered that scanning cattle a short time after transport generally leads to thermographs as follows:

(1) Thermographs of "normal" animals—The pixel count is higher in the test range than outside the test range.

(2) Thermographs of "stressed" animals—The animals have either cooler or warmer thermographs, that is, the proportion of the pixels above or below the test range is higher than the proportion of the pixels within the test range.

Scanning cattle more than about 6 hours after transport resulted in only two general types of thermographs, the "normal" thermographs and the "cooler" thermographs (i.e. the stressed animals had cooled such that their thermographs showed a higher proportion of the pixels below the test range than within the test range).

For cattle, a dorsal view was most preferred. This is likely also the most accessible and economical view. However, side views were also efficaceous. The most revealing anatomical site was the dorsal surface between the atlas and thoracic vertebrae. However, side views of trunk, head and extremities were also efficaceous.

Scanning swine by infrared thermography showed that a dorsal view was most preferred. The most revealing anatomical sites included the dorsal area between the atlas and thoracic vertebrae, most preferably including the intrascapular area between the atlas and cervical vertebrae.

The test temperature range found to be most efficaceous for swine was 24°–26° C. ±2° C. Normal, or low stress swine had a higher proportion of the IR scan (pixel count) in this test range. Stressed animals (or animals most likely to produce PSE pork) had IR thermographs with a higher proportion of the scan (pixel count) above this test range. Stressed swine tend to appear warmer (rather than cooler) in the thermographs.

While the IR detection method of this invention is preferably practised with computer data analysis, for accuracy, it is also amenable to practise by visual analysis. Distinctive colours or grey tones may be assigned by computers to the test temperature ranges of the scan and to the non-test temperature ranges (preferably every 1°–2° temperature range has a different colour). The thermographs are displayed on a computer monitor, such that a human operator can determine the animals having thermographs outside and/or inside the test temperature ranges.

Detected animals likely to produce degraded meat quality may be marked, or isolated for later treatment or lower sale value.

The method of the invention is illustrated in the following non-limiting examples:

EXAMPLES

To develop the detection method of the present invention, the inventors simulated the management and transportation practices normally experienced by market cattle. For example, a producer may transport cattle directly to an abattoir. Alternatively, a producer may transport cattle to an auction mart, and leave them overnight in lairage for sale the next day. After sale, the animals might be shipped again to a feedlot or to an abattoir, where they might be left again overnight. Thus the timing between the feedlot, transport and slaughter might be anywhere from an hour to several days. The timing affects the thermographic image of the animal.

EXAMPLE 1

This example reports early work with cattle using infrared scans taken us total animal side views just prior to stunning. In this example, 30 steers and 21 heifers (1 to 1.5 years old) were penned separatley, fasted for 24 hours, and divided into three treatment groups. The control group, Treatment 1, was not mixed by sex before being transported 3 km to the research centre. Including time in lairage, the animals were off feed for 24 hours. The second group, Treatment 2, was mixed by sex and transported for 320 km (6 hours) prior to a lairage period of 18 hours. Animals were off feed for 48 hours altogether. The third group, Treatment 3, was treated the same as Treatment 2, except that the animals received an additional 320 km (6 hours) of transport and were in lairage for another 18 hours. They were off feed for a total of 72 hours. Following the lairage period, animals were stunned and slaughtered at the Research Centre where carcass composition and meat quality were analyzed.

Infrared pictures or scans were taken of each animal just prior to stunning. The infrared thermal images (scans or thermographs) were taken with an Agema model 782 camera (AGA, Lidingo, Sweden). Subsequent resolution and printing of the individual thermographs was accomplished using Viewscan software (Viewscan Ltd, Concord, Ontario, Canada) as set out below.

The video signal from the camera was converted to digital data with a A/D converter before being processed by a computer as follows. The image was saved as a raw, uncalibrated data file. The area of the image itself was divided into 7140 pixels or pieces of information. The raw pixel data was digital data proportional to voltage signals from the IR camera. In order to analyze the thermograph, the digital data was converted to temperature data using a calibration procedure with the Viewsoft software. After calibration, the pixels were displayed in fifteen different colours plus a background colour, representing fifteen temperature ranges of 1.2°±0.2° C., ranging from 15.0° to 32.0° C.

The Viewsoft software allowed for analysis of the pixel data by different zones or by the entire image. Seven zones were identified as: Zone 0—whole image, including background, Zone 1—whole body of animal excluding background, Zone 2—trunk of the animal excluding extremities, Zone 3—front trunk from the shoulders to the midline, Zone 4—back trunk from the midline to the tail, Zone 5—head and neck, and Zone 6—extremities, including legs and tail. The following information was obtained for each zone using the Viewsoft software; absolute pixel counts and pixel counts as a percentage of the total pixels in the zone falling into each temperature range; maximum and minimum temperatures in the zone; the overall range of temperatures in the zone; the median, the mean, and standard deviations of temperatures in the zone; the total area of the zone (in pixels); and the area of the zone as a percentage of the total image area. The temperatures were grouped into larger temperature ranges to analyze the data. The four temperature ranges were: (1) 10.0–18.0, (2) 18.0–23.0 (3) 23.0–28.0 and (4) 28.0–36.0. The temperatures in each body zone were grouped into the four ranges. The number of pixels falling into each range was expressed as a percentage of the total number of pixels in that zone.

Since heat loss from the body surface may vary with location on the body, the thermograph of the amimal's body was divided into three zones for analysis, the trunk, the head, and the extremities. In each body zone, the area covered by each temperature range was expressed as a percentage of the total visible area.

As is evident from FIGS. 1–4, the three treatments resulted in different thermographic patterns. The animals with the greatest degree of transport stress had the greatest proportions of pixels counts in the cooler ranges.

The cattle with the greatest level of stress also showed altered meat quality traits observed as objective colour and shear values. The meat quality assessment was conducted according to the methods described by Jones et al., 1988. The cattle with the most degraded meat quality were those which had received the greatest stresses. The meat quality data is set out in Table 1.

TABLE 1

Effect of transport and handling in market weight cattle on the objective colour and shear values (toughness)

| Meat Quality Value | Treatment | | |
|---|---|---|---|
| | 1 | 2 | 3 |
| Shear (kg) | 5.08a | 6.75b | 8.23b |
| Colour | | | |

TABLE 1-continued

Effect of transport and handling in market weight cattle on the objective colour and shear values (toughness)

| Meat Quality Value | Treatment | | |
|---|---|---|---|
| | 1 | 2 | 3 |
| $L^*$ | 38.03a | 36.73 b | 36.02b |
| $a^*$ | 18.50a | 17.88ab | 17.27b |
| $b^*$ | 14.25a | 13.14 b | 12.88b |

Note: a,b $P<0.05$
($*$ C.I.E. colour system)

EXAMPLE 2

This example is included to demonstrate the efficacy of the method of the present invention in detecting poor meat quality in swine using infrared thermography. The IR scans were taken wiht a Thermovision 750 Serial #1066 camera with a 7 and 0 degree angle lens. Temperature measurements were made with a Taylor 9200 digital thermometer fitted with either a type J surface contact probe or an Exergen Microscanner to facilitate videorecording and electronic capture. Viewsoft version 2.00 software was used to analyze the thermographs.

Trial 1

Both barrows and gilts were used in this experiment. Two IRT scan procedures were used on the pigs. The first IRT image (A) was made of the pigs as they left their home pens. At this time the pigs were not mixed and were unstressed. The second image (B) was made of the pigs after they had been mixed with unfamiliar pigs and moved around the barn. This mixing and moving of pigs is common in the industry and constitutes a stress to the animals. The thermal images of the pigs were taken while the animal was in a small holding pen (squeeze). The animal was viewed from above and behind at a distance of approximately 0.7 meters with the 20 degree lens. The most revealing and useful angle scans were taken of the back and head enfilading at the spine at an angle of more than 45 degrees from the horizontal. The images were interfered in the neck or cervical region by a crossbar, visible in the thermographs.

The thermographs of 4 animals, with colours or grey tones assigned to temperature ranges, are shown in FIGS. 5A, 5B, 6A and 6B. Although the crossbar interfered with the image (shown as a white bar), it is evident that the animals receiving the greater stress had temperatures elevated above the 24°–26° C. range in the dorsal surface, specifically between the atlas and the cervical vertebrae, including the intrascapular area. The temperatures range in the thermographs was 21.7°–28.1° C., with 0.5° C. increments. The blue and purple temperature ranges were between 22.7 ° and 24.1° C. The black and dark green ranges were between 24.1 and 25.0. The light green ranges were between 25.0 and 25.9. The yellow range was between 25.9 and 26.4. The orange, bright purple and red ranges were between 26.4 and 28.1° C. With grey tones, the cooler temperatures were assigned darker tones and the warmer temperature were assigned gradually lighter tones.

Trial 2

The purpose of this trial was to confirm the site specificity of heat production as was suggested by the above trial. This trial also tested this specificity in pigs known to produce a high incidence of poor meat quality when subjected to antemortem stress. The degree of stress induced in the pigs in this trial was controlled by the direct manipulation of stress hormones (adrenergic agonists).

The pigs in this trial were genetically stress-susceptible or halothane positive pigs (H+phenotype, nn genotype) as defined by Sather et al., 1989. These pigs are known to produce a high incidence (80%) of poor meat quality traits, including pale colour, soft, texture, exudative or high drip-loss pork and low pH (Murray et al., 1986).

The pigs were fitted with indwelling ear-vein catheters under aseptic conditions 24 hours prior to endocrine studies. On the day of experiments the pigs were anaesthetized with ketamine (Ketalar) at 20 mg per kg animal weight in accordance with guidelines established by the Canadian Council on Animal Care. It should be noted that ketamine anaesthesia was necessary in that a respiratory anaesthetic such as halothane would have induced malignant hyperthermia in these pigs. Following anaesthesia the pigs received an intravenous infusion of selected adrenergic agonists including dobutamine (Dobutrex, B1, 5.6 ug/kg/min for 30 minutes), and Clenbuterol (B2, 3.39 ug/kg/min for 30 minutes). In anaesthetized pigs, a series of sub cutaneous thermocouples (inserted approximately 2 cm) were placed along the spine from the cervical to the lumbar areas. These thermocouples were connected to a data-logger which recorded direct temperature readings every 30 seconds.

The results are shown in FIGS. 7–12, as plots of changes in the neck thermocouple temperatures (%) with time in relation to the start of infusion of the adrenergic agonists. (In the FIGS., the numbers 92108 and 91208 etc. indicate different animals) The Figures show that a direct and controlled challenge of adrenergic agonists (stress hormones) in pigs known to produce poor quality pork was accompanied by an increase in the thermocouple temperature, particularly in the cervical (and occasionally lumbar but not thoracic) areas of the dorsal surface of the pig. This increase in temperature is consistent with the above trial showing IRT temperature increases in these same anatomical areas. The data also confirms that these thermal changes coincide with the production of poor pork quality, as the halothane positive pigs used in this trial are documented to produce approximately 80% poor pork quality.

EXAMPLE 3

This example illustrates the detection method of this invention using dorsal IR thermographs of bulls taken directly after transport. The camera and computer software were as in Example 1.

In this example data was collected on 54 crossbred yearling bulls weighing on average 500 kg. The animals had been raised on a conventional balanced silage-cereal grain diet with ad libitum access to water and iodized salt. The cattle were allocated to one of two treatments, balanced by breed and weight and designated as control or treated. The control animals remained on their normal diets and with familiar pen mates until the morning of the experiment. The cattle were then moved to a weighing facility, weighed, loaded onto a commercial cattle liner and transported a short distance (3 km) to the abattoir. The bulls were then unloaded into abattoir lairage pens, measuring approximately 3 m by 10 m for ½ to 2 hours before being scanned from above with an infrared thermography camera (as Ex. 1). The camera was placed approximately 2 m above the back of the animal and the scan was taken at approximately a 75 degree angle. Within 2 to 3 hours of being scanned, the animals were moved on into the abattoir premise and slaughtered as per conventional commercial practice.

Figure 13:
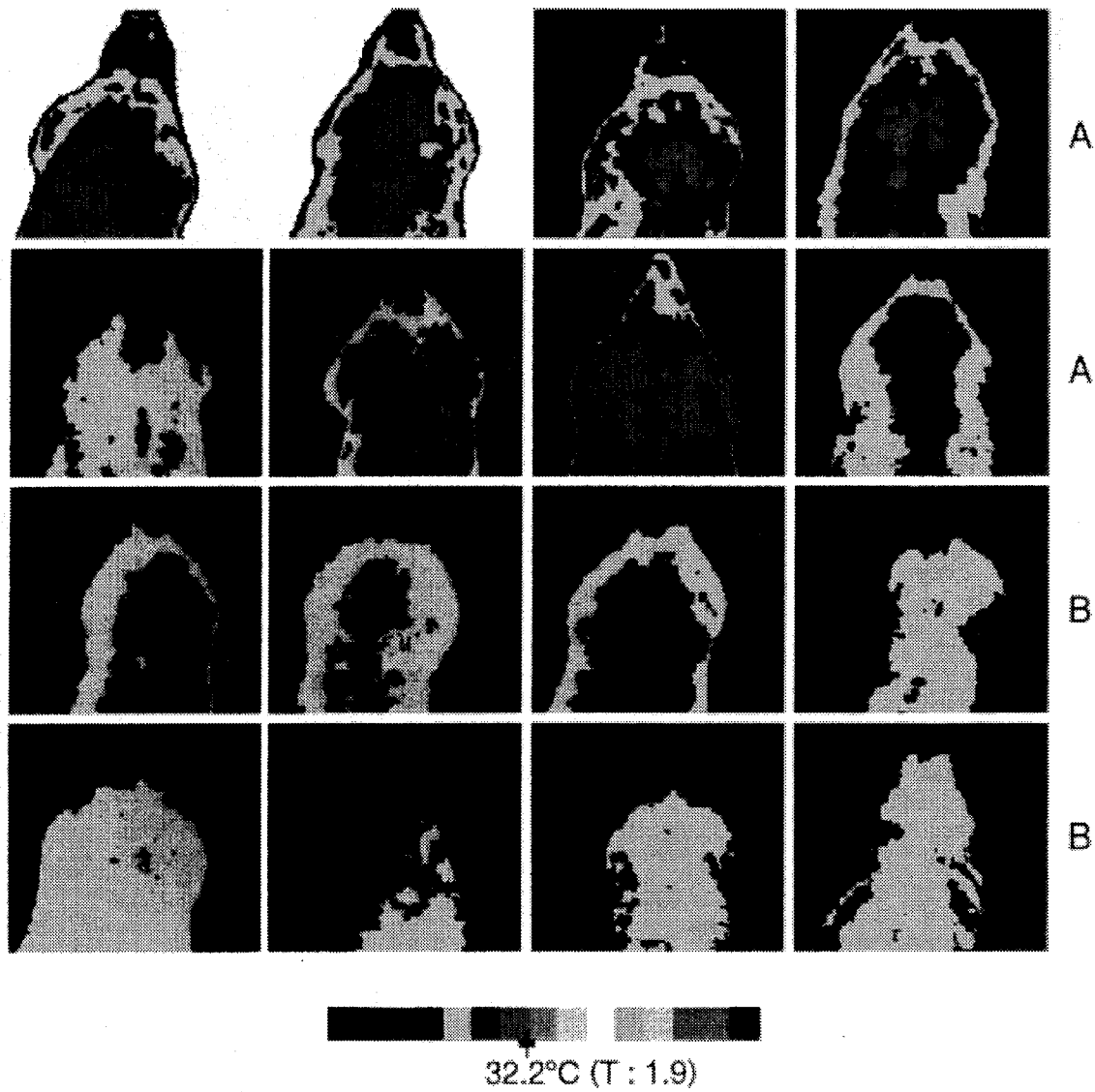
FIGS. 13 and 14 are IR thermographs taken as dorsal views of thirty two cattle prior to slaughter, graphs A denoting animals with highest pixel counts in the 28°–32° C. range and graphs B and C denoting animals with highest pixel counts below and above the this temperature range, respectively.
Figure 14:
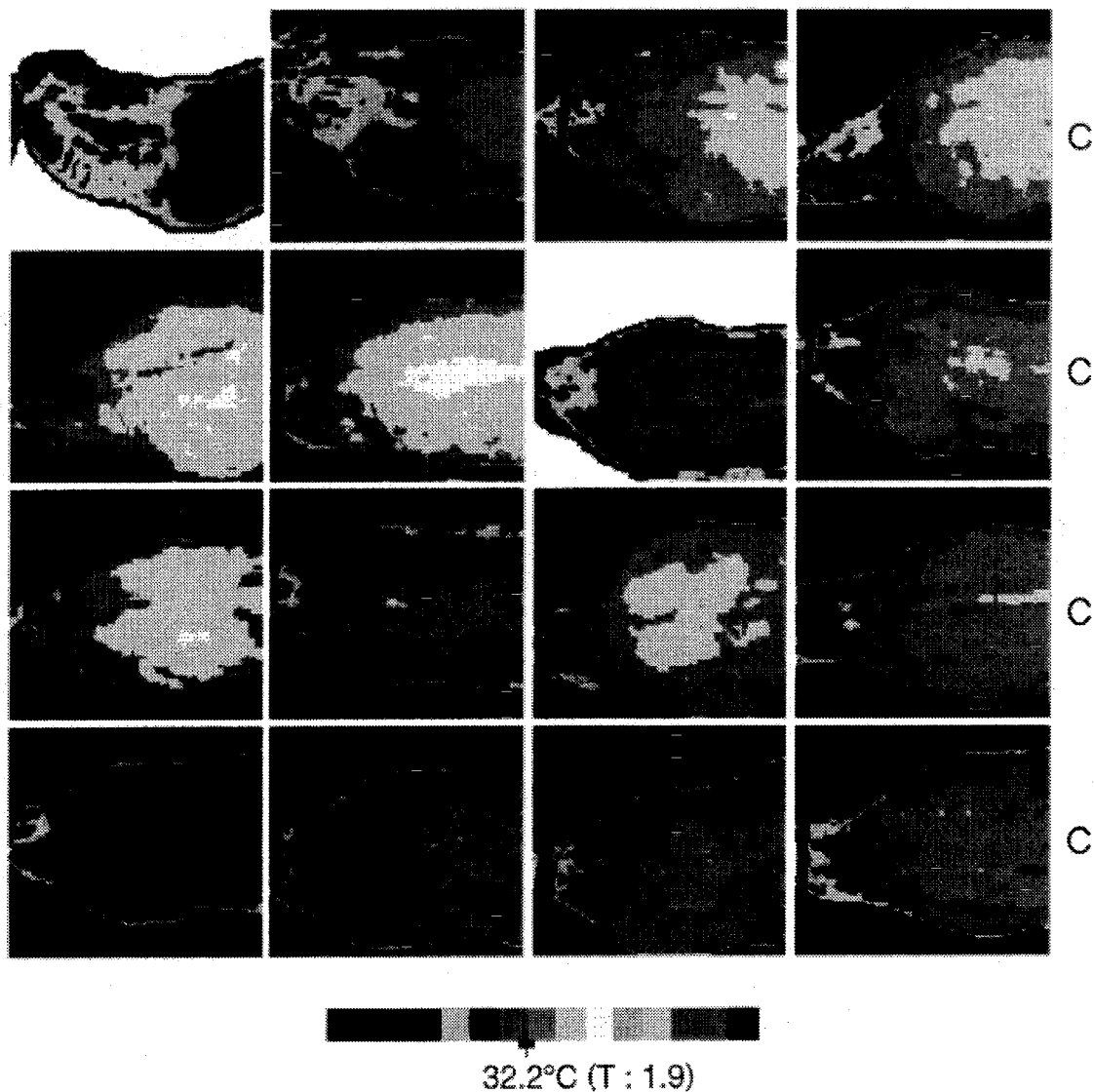

The treatment animals were taken off of feed and water 24 hours before transport. In addition, the bulls were mixed from a minimum of 2 different and unfamiliar pens of cattle. These time off feed and mixing conditions are common in auction mart and some feedlot operations, and constitute a stress to the animals. The treatment bulls received one hour of transport following morning weight collections. Once unloaded in the abattoir/lairage area the infrared scanning and slaughter procedures were completed in an identical manner to the control animals. Meat quality data was assessed as per the Canadian grading system (Dark cutters grading D4, or B2 under the pre-1993 regulations formerly a grade of B2 prior to institution of the new beef grading system in 1993). The thermographs are shown in FIGS. 13 and 14 for 32 animals, and were analyzed as set out below.

For animals in this study, 11 temperature ranges in were examined. These ranges (°C.) were as follows: 1=10.0–18.9; 2=18.9–20.8; 3=20.8–22.7; 4=22.7–24.6; 5=24.6–26.5; 6=26.5–28.4; 7=28.4–30.3; 8=30.3–32.2; 9=32.2–34.1; 10=34.1–36.0; 11=36.0–37.9.

Following statistical analysis of the data, it was learned that:

(a) greater than 80% of the treated cattle produced carcasses designated by the grading system as being B4 dark cutters;

(b) 40% of the pixel area from the control animals, but only 12% of the pixel areas of the treated animals, fell into temperature range 7;

(c) 30% of the pixel area of the control animals, but only 16% of the pixel area of the treated animals, fell into temperature range 8.

The thermographs of 32 animals are shown in FIGS. 13 and 14. Animals within the temperature ranges 7 and 8, that is with higher pixel numbers in those ranges than outside those ranges in Group A. All of the animals in Group A proved to produce normal or non-dark cutting meat, with the exception of one animal, which proved to be a dark cutter. Groups B and C thermographs show animals outside the temperature ranges 7 and 8, that is with higher pixel counts outside the ranges than inside the ranges. Group B thermographs were below (cooler than) the temperature ranges 7 and 8, while Group C thermographs were above (warmer than) the temperature ranges 7 and 8. All of the animals whose thermographs are shown in groups B and C proved to produce darker coloured meat (dark cutters) (with the exception of one animal (of the 24 in B and C)). By assigning colours or grey tones to the ranges, one is able to readily visually determine which animals are predominantly within or without the temperature ranges.

It is thus apparent that the majority of treated (stressed) cattle had a lower proportion of pixels in the ranges 7 and 8, and a higher proportion of pixels in the hotter or colder temperatures outside these ranges. Thus animals having a lower number of pixels in the temperature ranges 7 and 8 were more likely to be stressed and had a higher probability of poor meat quality.

LIST OF REFERENCES

Clark, J. A. and Cena, K. 1972. Thermographic measurements of the surface temperatures of animals, J. of Mammalogy 54:1003–1007.

Lamarque, J. L., Senac, J. P., Russi, M., Pasqual, J., Respand, G. 1975, Romieu, M. and Jordan, J. Etudthermographicque experimentale en pathologic artevielle peripherique. Ann. Radiol. 18:513–523.

Kenny, F. J. and Tarrant, P. V. 1987. The physiological and behavioural responses of crossbred Friesian Steers to shorthaul transport by road. Lives. Prod. Sci. 17:63–75.

Stephens, D. B. 1980. Stress and its management in domestic animals: A review of behavioural and physiological studies under field and laboratory situations. Adv. Vct Sci. Comp. Med. 24:179–210.

Frens, J. 1975. The influence of skin temperature on thermoregulation. In N. J. M. A. Tilburg.

M. G. Strasbourg and E. F. J. R. Both (Ed.) Thermography. S. Karger, Basel P. 218–223.

Houdas, Y. and Guieu, J. D. 1975. Environmental Factors affecting skin temperatures. In. N. J. M. A. Tilburg, M. G. Strasbourg and E. F. J. R. Both (Ed.) Thermography. S. Karger, Basal P. 157–165.

Jones, S. D. M., Schaefer, A. L., Tong, A. K. W., and Vincent, B. C., 1988. The effects of fasting and transportation on beef cattle. 2. Body component changes, carcass composition and meat quality. Lives. Prod. Sci. 20:25–35.

Warris, P. 1986. Live animal marketing effects on carcass and meat quality. Proceedings P 7–41. In. Work Planning Meeting and meat quality. Agric. Can. R. P. S., Ottawa.

Gariepy, C. J., Amiot, J. and Nada, S. 1987. Early prediction of PSE and DFD by infrared thermography on Live animals. Proc. 33rd Int. Cong. Meat Sci. Tech. II 403–405.

Schaefer, A. L., Jones, S. D. M., Tong, A. K. W., and Vincent, B. C. 1988. The effects of fasting and transportation on beef cattle. 1. Acid-base—electrolyte balance and infrared heat loss of beef cattle. Lives. Prod. Sci. 20:15–24.

Schaefer, A. L., Jones, S. D. M., Murray, A. C., Sather, A. P., and Tong., A. K. W. 1989. Infrared thermography of pigs with known genotypes for stress susceptibility in relation to pork quality. Can. J. Anim. Sci. 69:491–495.

Schaefer, A. L., Jones, S. D. M., Tong, A. K. W., and Vincent, B. C. 1987a. The effects of fasting and transport on acid-base balance, infrared heat loss and muscle quality of beef cattle. Can. J. Anim. Sci. 67:1182.

Schaefer, A. L., Jones, S. D. M., Murray, A. C., Sather, A. P., and Tong, A. K. W. 1987b. Infrared thermography in three lines of pigs. Can. J. Anim. Sci. 67:1181.

Haywood, J. A., Eckerson, J. D. and Collis, M. 1975. Thermal balance and survival time prediction of men in cold water. Can. J. Physiol. Pharmacol. 53:21–32.

Jones, S. D. M. and Tong, A. K. W. 1989. Factors influencing the commercial incidence of dark cutting. Can. J. Anim. Sci. 69:649–654.

Sather, A. P. and Murray, A. C. 1989. The development of a halothane sensitive line of pigs. Can. J. Anim. Sci. 69:323–331.

Murray, A. C. and Sather, A. P. 1986. Characteristics of the meat quality of a halothane-positive line of swine. Can. J. Anim. Sci. 66:1168.

All publications mentioned in this specification are indicative of the level of skill of those skilled in the art to which this invention pertains. All publications are herein incorporated by reference to the same extent as if each individual publication was specifically and individually indicated to be incorporated by reference.

Although the foregoing invention has been described in some detail by way of illustration and example for purposes of clarity of understanding, it will be obvious that certain changes and modifications may be practised within the scope of the appended claims.

We claim:

1. A method for detecting a high probability of producing poor meat quality in live domestic cattle, comprising:

scanning an area of a live animal with an infrared camera to produce a thermographic image;

determining the proportion of the image falling within a test temperature range of 28°–32°±2° C.;

determining the proportion of the image falling outside the test temperature range of 28°–32°±2° C.; and rejecting the animal as one having a high probability of producing poor meat quality if the proportion of the image falling within the test temperature range is lower than the proportion of the image falling outside the test temperature range.

2. The method as set forth in claim 1, wherein the proportions of the image falling within the test temperature range and the proportion of the image falling outside the temperature range are determined as respective proportions of the total pixel count for the area of the animal scanned.

3. The method as set forth in claim 2, wherein the animal is scanned after about 6 hours of transport to the antemortem environment, and wherein the method further comprises determining the proportion of the image falling below the test temperature range of 28°–32°±2° C.; and rejecting the animal as one having a high probability of producing poor meat quality if the proportion of the image falling within the test temperature range is lower than the proportion of the image falling below the test temperature range.

4. The method as set forth in claim 1, wherein the animal is scanned in an antemortem environment.

5. The method as set forth in claim 4, wherein the animal is scanned within about 6 hours of transport to the antemortem environment.

6. The method as set forth in claim 4, wherein the animal is scanned from the side.

7. The method as set forth in claim 6, wherein the animal is scanned in at least one area selected from the group consisting of the head, trunk and extremities.

8. The method as set forth in claim 7, wherein the test temperature range is 28°–32° C.

9. The method as set forth in claim 8, wherein the animal is beef cattle.

10. The method as set forth in claim 4, wherein the dorsal surface of the animal is scanned.

11. The method as set forth in claim 10, wherein the animal is scanned between the atlas vertebrae and the thoracic vertebrae.

12. The method as set forth in claim 1, wherein the test temperature range is 28°–32° C.

13. The method as set forth in claim 1, 11 or 12, wherein the animal is beef cattle.

14. A method for detecting a high probability of producing poor meat quality in live domestic swine, comprising;

scanning an area of a live swine animal with an infrared camera to produce a thermographic image;

determining the proportion of the image falling within a test temperature range of 24°–26°±2° C.;

determining the proportion of the image falling outside the test temperature range 24°–26°±2° C.; and rejecting the animal as one having a high probability of producing poor meat quality if the proportion of the image falling within the test temperature range is lower than the proportion of the image falling outside the test temperature range.

15. The method as set forth in claim 14, wherein the dorsal surface of the animal is scanned.

16. The method as set forth in claim 15, wherein the animal is scanned between the atlas vertebrae and the thoracic vertebrae.

17. The method as set forth in claim 15, wherein the animal is scanned between the atlas vertebrae and the cervical vertebrae.

18. The method as set forth in claim 15, wherein the animal is scanned in the intrascapular area between the atlas vertebrae and the cervical vertebrae.

19. The method as set forth in claim 18, wherein the test temperature range is 24°–26° C.

20. The method as set forth in claim 19, which further comprises determining the proportion of the image falling above the test temperature range of 24°–26° C. and rejecting the animal as one having a high probability of producing poor meat quality if the proportion of the image falling within the test temperature range is lower than the proportion of the image falling above the test temperature range.

* * * * *